DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED OCTOBER 13, 1970

879 O.G. 365

T879,002

OLEFIN OXONATION PROCESS

William L. Senn, Jr., 850 E. Lakeview Drive 70810, and Joseph K. Mertzweiller, 9266 N. Parkview Drive 70815, both of Baton Rouge, La., and Michael D. Bentley, Ledge Hill Road, Orono, Maine 04473

Filed Dec. 29, 1969, Ser. No. 888,848

**Int. Cl. C07c *45/10***

U.S. Cl. 260—604

No Drawing. 18 Pages Specification

Essentially linear alcohol and aldehyde products can be prepared by reacting an olefinic compound, such as propylene, butene, octene-1, etc., with carbon monoxide and hydrogen at elevated temperatures and pressures in the presence of a catalyst comprising (a) a Group VIII metal compound in complex bond with carbon monoxide and a biphyllic ligand and (b) the reaction product of a metal having an atomic number from 22–25 and a biphyllic ligand. The preferred biphyllic ligands are triorgano phosphorus and arsenic compounds, such as tributyl phosphine. Component (a) of the catalyst system desirably possesses the general formula $M(CO)_3XR_3$, $[M(CO)_3XR_3]_2$ or $C_nH_{2n-1}M(CO)_2XR_3$ wherein M is a Group VIII metal, X is a phosphorus or arsenic atom, R is a $C_1$–$C_{20}$ alkyl or alkoxy radical and $n$ is an integer varying from 4 to 7. The alcohol and aldehyde compounds are prepared at a temperature varying from about 200–500° C. and at a carbon monoxide and hydrogen pressure varying from 300–3000 p.s.i.g. The catalyst system can be formed in situ during the course of the oxonation reaction by contacting a Group VIII metal chelate or soap, a chelate or soap of metal having the atomic number varying from 22–25 and a biphyllic ligand with carbon monoxide and hydrogen in the reaction zone in the further presence of the olefinic feedstock and process solvent. The preferred Group VIII catalyst metal is cobalt and the preferred metal having an atomic number of from 22–25 is manganese.